(12) United States Patent
Napolitano et al.

(10) Patent No.: US 8,517,897 B2
(45) Date of Patent: Aug. 27, 2013

(54) SYSTEM AND METHOD FOR PROMOTING AND TRACKING PHYSICAL ACTIVITY AMONG A PARTICIPATING GROUP OF INDIVIDUALS

(75) Inventors: Frank Napolitano, Philadelphia, PA (US); Andrew Greenberg, Philadelphia, PA (US); Christian Ludwig, Philadelphia, PA (US)

(73) Assignee: GlobalFit, Philadelphia, PA (US)

( * ) Notice: Subject to any disclaimer, the term of this patent is extended or adjusted under 35 U.S.C. 154(b) by 0 days.

(21) Appl. No.: 13/280,954

(22) Filed: Oct. 25, 2011

(65) Prior Publication Data

US 2012/0042070 A1  Feb. 16, 2012

Related U.S. Application Data

(63) Continuation of application No. 12/411,383, filed on Mar. 25, 2009, now Pat. No. 8,070,655, and a continuation of application No. 13/276,299, filed on Oct. 18, 2011.

(51) Int. Cl.
| | |
|---|---|
| *A63B 71/00* | (2006.01) |
| *A61B 5/103* | (2006.01) |
| *A61B 5/117* | (2006.01) |

(52) U.S. Cl.
USPC ............................................. 482/8; 600/595

(58) Field of Classification Search
USPC ............ 705/2, 14.1; 434/247, 255; 600/300, 600/587, 595; 482/1–9, 901–902; 700/91–92
IPC ............ A63B 15/02, 71/00; A61B 5/103, 5/117
See application file for complete search history.

(56) References Cited

U.S. PATENT DOCUMENTS

| | | | | |
|---|---|---|---|---|
| 7,254,516 | B2 * | 8/2007 | Case et al. | 702/182 |
| 7,670,263 | B2 * | 3/2010 | Ellis et al. | 482/8 |
| 7,698,101 | B2 * | 4/2010 | Alten et al. | 702/182 |
| 7,901,292 | B1 * | 3/2011 | Uhlir et al. | 463/42 |
| 7,953,549 | B2 * | 5/2011 | Graham et al. | 701/466 |
| 2004/0198555 | A1 * | 10/2004 | Anderson et al. | 482/8 |
| 2006/0025282 | A1 * | 2/2006 | Redmann | 482/8 |
| 2006/0189440 | A1 * | 8/2006 | Gravagne | 482/8 |
| 2007/0032344 | A1 * | 2/2007 | Guo | 482/8 |
| 2007/0142179 | A1 * | 6/2007 | Terao et al. | 482/8 |
| 2007/0208531 | A1 * | 9/2007 | Darley et al. | 702/142 |
| 2008/0090703 | A1 * | 4/2008 | Rosenberg | 482/8 |
| 2008/0096726 | A1 * | 4/2008 | Riley et al. | 482/8 |
| 2008/0153670 | A1 * | 6/2008 | McKirdy et al. | 482/1 |
| 2008/0214903 | A1 * | 9/2008 | Orbach | 600/301 |
| 2008/0221928 | A1 * | 9/2008 | Garcia et al. | 705/3 |
| 2008/0258921 | A1 * | 10/2008 | Woo et al. | 340/573.1 |
| 2010/0056872 | A1 * | 3/2010 | Kahn et al. | 600/300 |
| 2010/0105525 | A1 * | 4/2010 | Thukral et al. | 482/8 |
| 2010/0125028 | A1 * | 5/2010 | Heppert | 482/8 |
| 2010/0144414 | A1 * | 6/2010 | Edis et al. | 463/8 |
| 2010/0184564 | A1 * | 7/2010 | Molyneux et al. | 482/1 |

* cited by examiner

*Primary Examiner* — Oren Ginsberg
(74) *Attorney, Agent, or Firm* — Barnes & Thornburg LLP; Thomas J. McWilliams; Edward F. Behm, Jr.

(57) ABSTRACT

A system and method of tracking physical activity of a person in order to help motivate that person to add more exercise to their lives. Each participant is provided a motion sensor that detects forces incurred by the participant. The motion sensor creates electronic data that corresponds to the forces detected. The data is analyzed to determine whether or not exercise has been performed. The analysis can also determine the type of exercise performed, when the exercise was performed, and the duration of the exercise performed.

5 Claims, 5 Drawing Sheets

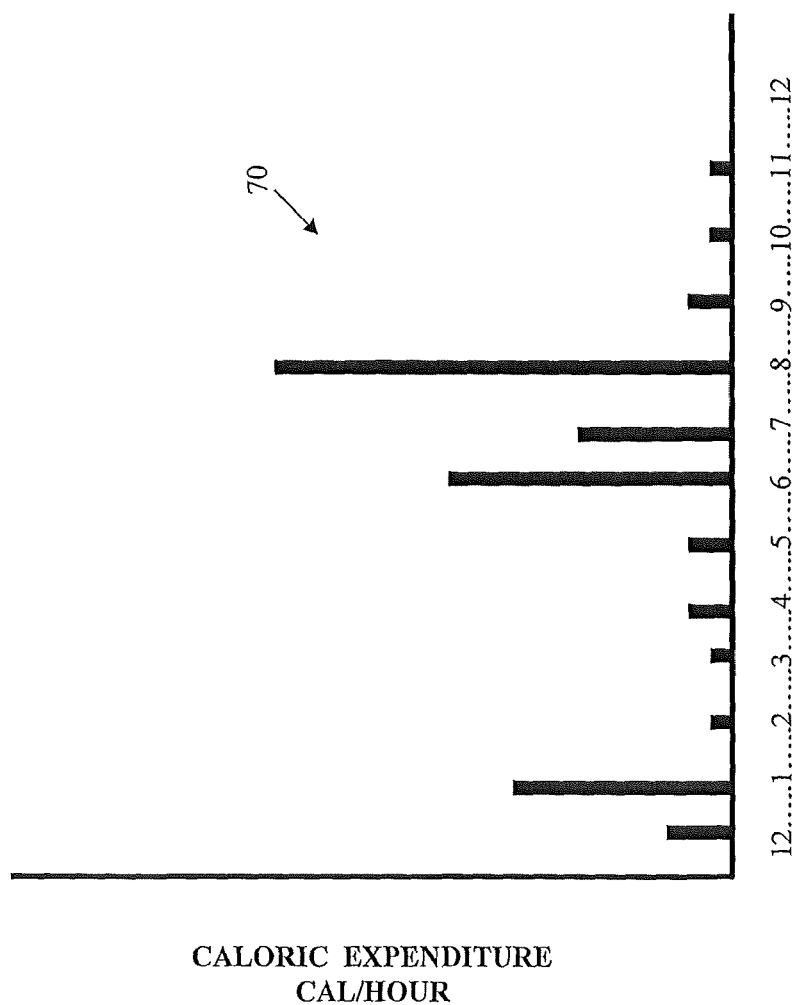

SYSTEM AND METHOD FOR PROMOTING AND TRACKING PHYSICAL ACTIVITY AMONG A PARTICIPATING GROUP OF INDIVIDUALS

CROSS-REFERENCE TO RELATED APPLICATION

This application is a continuation of U.S. patent application Ser. No. 12/411,383 now U.S. Pat. No. 8,070,655 entitled, "System and Method for Promoting and Tracking Physical Activity Among a Participating Group of Individuals," filed Mar. 25, 2009, and a continuation of U.S. patent application Ser. No. 13/276,299 entitled, "System and Method for Promoting and Tracking Physical Activity Among a Participating Group of Individuals," filed Oct. 18, 2011, the contents of which are hereby incorporated by reference as if set forth in their entirety.

BACKGROUND OF THE INVENTION

1. Field of the Invention

In general, the present invention relates to systems and methods that are used to track the health and wellbeing of people within a targeted group. More particularly, the present invention relates to systems and methods that utilize interactive software to both promote and track physical activity among participants in the targeted group.

2. Description of the Background

It is a well-established fact that people generally live longer, healthier lives if they exercise regularly. It is also a well-established fact that people are more likely to start and continue an exercise program if they have peers and friends that are also participating in that exercise program. Recognizing the above stated facts, many companies have developed employee exercise programs. The hope is that these programs would lead to healthier employees and healthier employees would use less sick days and have lower healthcare costs. By offering exercise such programs at work, it is hoped that employees would exercise with peers and would benefit from the support of peers.

Difficulties develop, however, when the management of a company tries to develop exercise programs for their employees. The problem is that not all people enjoy the same types of exercise. As such, a company gym may only appeal to some employees, while a company softball team may appeal to others. Recognizing that different people like different things, exercise programs have been developed that are highly flexible to fit the varied needs and wants of a company's employees. In such exercise programs, the management of a company does not concern itself with what exercise is being performed. Rather, the company just monitors whether exercise is being performed and offers incentives to employees to continue exercising.

The most common way that companies monitor whether or not an employee is performing exercise is to provide the employees with interactive computer software. Using the software, an employee can enter what exercise has been performed. This information is then stored in a database for access by the company. Such exercise monitoring software systems are exemplified by U.S. Patent Application Publication No. 2006/0287883 to Turgis, entitled Interactive Internet Supported Health And Fitness Management System; U.S. Patent Application Publication No. 2007/0072154 to Kaufman, entitled Lifesytle Coach Behavior Modification System; and U.S. Patent Application Publication No. 2007/0100595 to Earles, entitled Behavior Monitoring And Reinforcement System and Method.

The problem associated with such prior art exercise monitoring software systems is that the systems require that an individual manually input data into a computer to inform the computer of what exercise has been performed. Since many of these systems provide rewards for exercise, there is a good incentive for people to lie about exercising or exaggerate in order to receive the reward. Furthermore, people quickly grow tired of tasks in which they are not interested. Employees that must voluntarily enter and log their daily exercise routines may quickly develop user fatigue. Employees may forget to enter data daily and when they do enter data, that data may contain guesses and inaccurate remembrances of days past.

Another problem associated with such prior art exercise systems is that it is difficult for an employee to equate different exercises with one another. For example, how may miles of kayaking equate to how many hours of playing tennis? This difficultly in equating exercises makes it very difficult to establish goals for rewards. It also makes it very difficult to set up challenges and competitions among participants that would promote further exercise.

A need therefore exists for an exercise system that both passively and accurately monitors the amount of exercise performed by an individual, thereby reducing cheating and user fatigue. A need also exists for an exercise system where all exercises are automatically reduced to comparable caloric expenditure units, thereby enabling all exercises to be compared for use in challenges and competitions. These needs are met by the present invention as described and claimed below.

SUMMARY OF THE INVENTION

The present invention is a system and method of tracking physical activity of a person in order to help motivate that person to add more exercise to their lives. Each participant is provided a motion sensor that detects forces incurred by the participant. The motion sensor creates electronic data that corresponds to the forces detected. The motion detector is worn by the participant at some point on the body both when the participant is exercising and when the participant is not exercising.

The motion sensor has the ability to passively transmit the data it collects. The data is analyzed. During the analysis of the data, it can be determined whether or not exercise has been performed. The analysis can also determine the type of exercise performed, when the exercise was performed, and the duration of the exercise performed.

The exercise of each participant can be converted into a preselected caloric expenditure unit for a specific type of exercise. In this manner, the exercise types of all participants can be accurately compared and applied to common exercise goals or exercise competitions. If an exercise goal is achieved, participants are rewarded with reward points in an amount proportionate to difficulties in achieving the exercise goal. The reward points can be used as payment for selected goods and services that promote a healthy lifestyle.

BRIEF DESCRIPTION OF THE DRAWINGS

For a better understanding of the present invention, reference is made to the following description of an exemplary embodiment thereof, considered in conjunction with the accompanying drawings, in which:

FIG. 5 is a graph plotting caloric expenditure against time for various detected exercises.

DETAILED DESCRIPTION OF THE INVENTION

Although the present invention system can be used by many different user groups, such as schools, health clubs, or a community of registered online users, the embodiment illustrated shows the system being used by an employer to promote exercise among its employees. This embodiment is selected in order to set forth the best mode contemplated for the invention. The illustrated embodiment, however, is merely exemplary and should not be considered a limitation when interpreting the scope of the appended claims.

Figure 1:
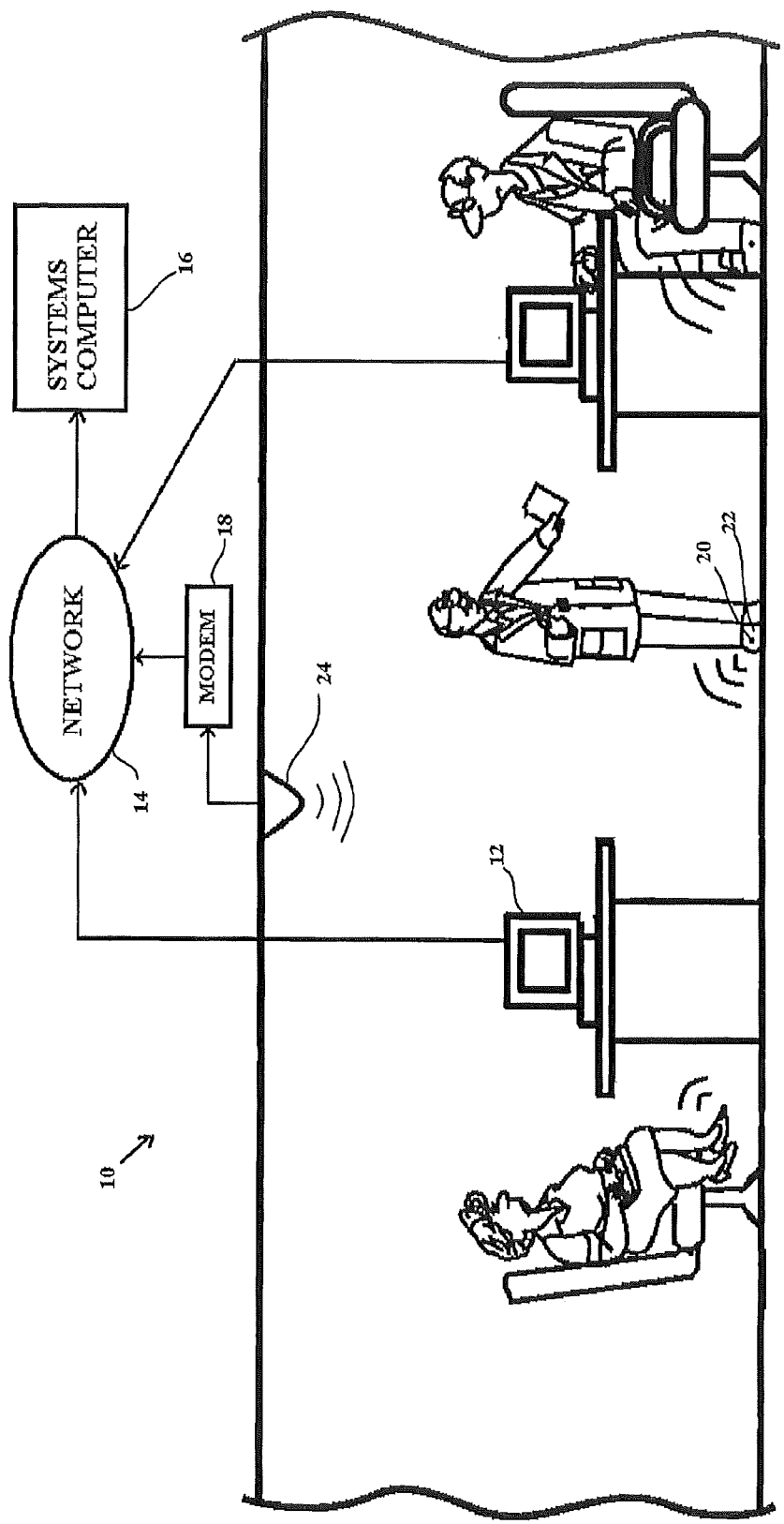
FIG. 1 is a schematic view of an office containing the present invention system.

Referring to FIG. 1, a segment of a traditional office 10 is shown in which employees work. The employees have computers 12 that are connected through a network 14 to a remote system computer 16. The network 14 can be private, but is expected to be connected to the Internet.

Each employee is provided with a monitoring unit 20. The monitoring unit 20 is worn on the body of the employee. Preferably, the monitoring unit 20 is connected to the shoe 22 of the employee. However, the monitoring unit 20 can also be connected to a sock, watchstrap, belt, or other such feature on a limb or waist of the employee. As will later be explained in more detail, the monitoring unit 20 records data corresponding to forces experienced by the monitoring unit 20 in a given time period. The data can be used to determine whether or not exercise has occurred. The data can also be used to determine the type of exercise performed and when that exercise was performed.

In the office 10, at least one transceiver 24 is installed. The transceiver 24 transmits an activation signal 26 that is received by any monitoring unit 20 within range. Once a monitoring unit 20 receives an activation signal 26, it transmits its stored data to the transceiver 24 along with an identifier code for the employee. The transceiver 24 receives both the identifier code and the transmitted data. That information is then forwarded to the remote system computer 16 via the same computer network 14.

The downloading of data from the monitoring unit 20 to the system computer 16 happens automatically each time an employee comes into the office 10. As such, the data transfer is passive, needing no effort from the employee. The employee need only remember to connect the monitoring unit 20 to a shoe or similar article of clothing being worn.

The system computer 16 utilizes the data from each employee to track what exercise has been performed by the employee and when. Many types of exercise can be identified by the system computer 16 through analysis of the type of data that is received. For instance, walking and running are easily identifiable. Other types of exercise can be identified as exercise, but the specific exercise may not be discernable. For instance, the data produced from playing tennis is nearly identical to the data produced from playing dodge ball. However, dodge ball generally burns more calories than does tennis.

When an employee logs onto his/her office computer 12, the employee may be actively prompted with a message that indicates the exercise system has received new data. Otherwise, the system may be passive and wait for an employee to log onto the exercise system. Once interacting with the exercise system, the employee can recall data in many formats to show when exercise was performed, what exercise was performed, and for how long. As will later be explained, the data can also be applied to selected exercise challenges and competitions.

If the exercise system has received data that it cannot positively identify, then the employee is prompted to identify the exercise. The employee is reminded of when the exercise was performed and for how long. The employee then is provided with a list of exercises from which to choose. The employee selects the exercise that best described the activity performed. The system computer 16 then has a complete set of data corresponding to the exercise activities of the employee.

To help motivate the employee, the exercise system 10 presents challenges and competitions to the employee. The system computer 16 then applies all exercise data to those challenges and competitions, in a manner later explained.

Figure 2:
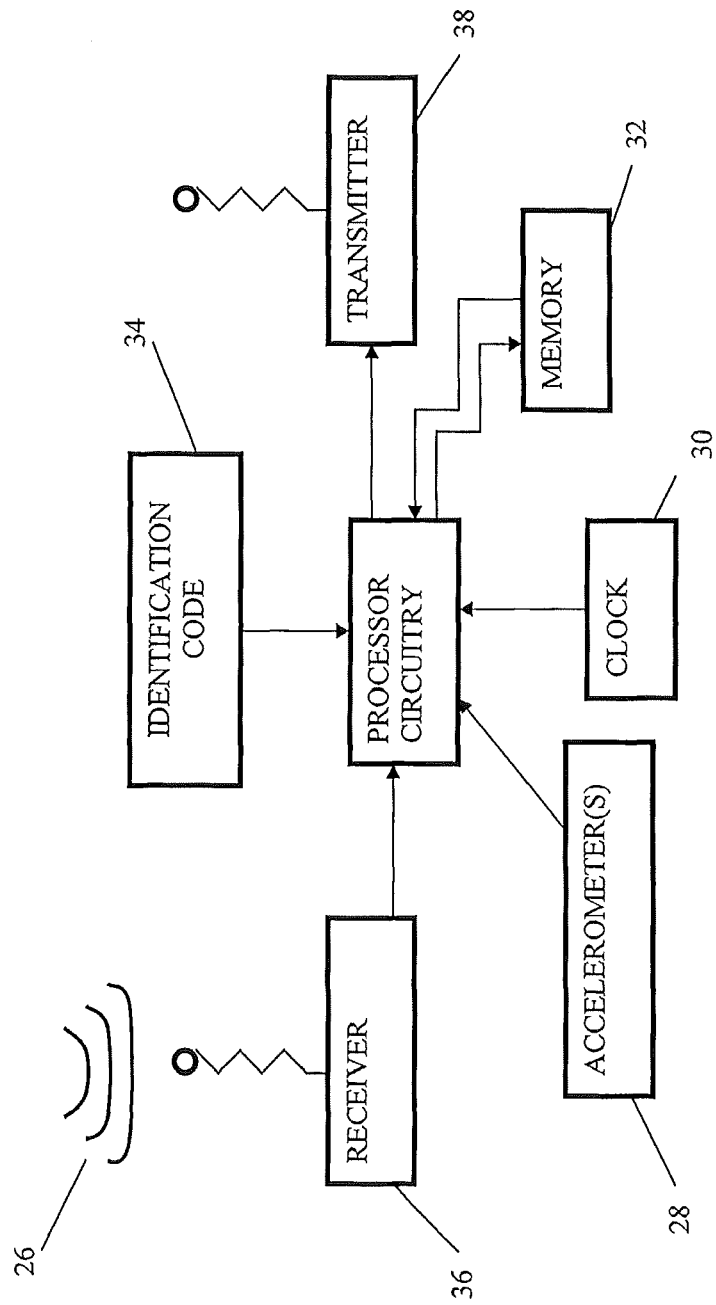
FIG. 2 is a schematic of an exemplary embodiment of a monitoring unit.

Referring to FIG. 2, a schematic of a monitoring unit 20 is shown. Each monitoring unit 20 contains at least one accelerometer 28. The accelerometers 28 are preferably microelectromechanical systems (MEMS), however other technologies can be used. The accelerometers 28 measure changes in acceleration in different orientation planes and convert that information into corresponding electronic signals. Within the monitoring unit 20, a clock 30 is provided. The clock 30 creates a time code signal that is coupled to each electronic signal produced by the accelerometers 28. The combined signals are stored in a memory 32 as data signals.

Each monitoring unit 20 has its own identification code 34 that identifies the monitoring unit 20. Each monitoring unit 20 also has a receiver 36 for receiving the activation signal (26, FIG. 1) and a transmitter 38 for transmitting both the data signals and the identification code 34. Suitable monitoring units 20 that can be adapted for use by this invention are manufactured by Fitlinxx, Inc. of Norwalk, Conn.

Figure 3:
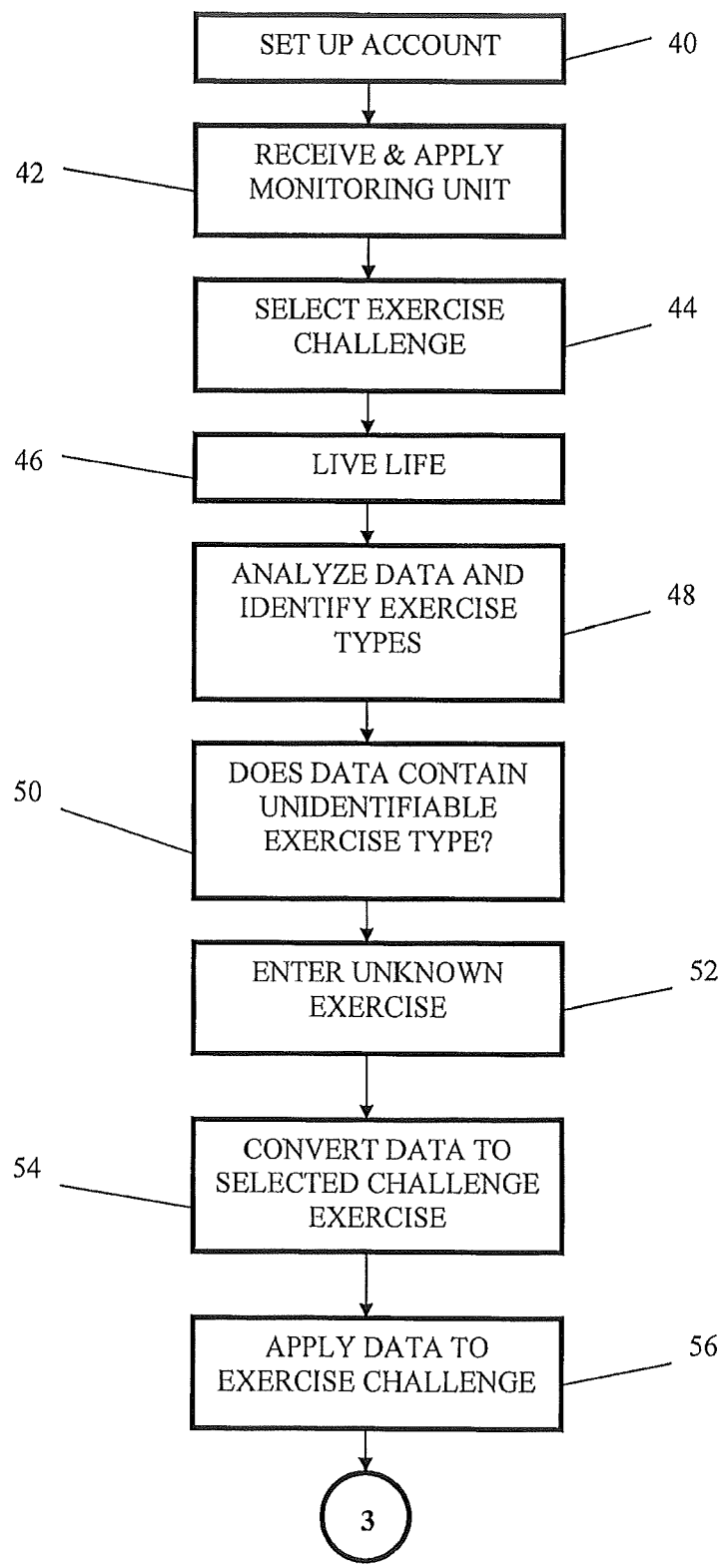
FIG. 3 is a block diagram showing a methodology of operation for the present invention system.

Referring now to FIG. 3 in conjunction with FIG. 1, the operational methodology of the system is described. As is indicated by Block 40, each participating employee is assigned an account number for accessing the system computer 16. Furthermore, each participating employees is provided with at least one monitoring unit 20. See Block 42. An employee may be given more than one monitoring unit 20. In this manner, the employee can attach a monitoring unit 20 to each of the sets of shoes he/she commonly wears. Within the system computer 16, the identification code 34 for each monitoring unit 20 given to an employee is assigned to the account for that employee.

Once an employee has set up an account, the employee is provided with a choice of exercise challenges from which to choose. See Block 44. For instance, one challenge may be a virtual hike. An employee, using their network computer 12, may select a geographical area, such as Pennsylvania, France, Kenya or the like. The systems computer 16 will then generate a virtual hiking tour. The systems computer 16 will then indicate how many steps are required to complete the virtual tour. For example, it may be 456,789 steps. The challenge, then, becomes for the employee to walk 456,789 steps. Each time the employee downloads data to the system computer 16, the data is converted to steps, if necessary, and applied to the challenge. The systems computer 16 may provide different images of different landmarks in the selected geographical area as data is applied to the challenge.

Other challenges may also be provided. For example, one employee may enter into direct competition with other employees to complete a stated amount of exercise in a stated amount of time.

Rewards may be provided to people who accomplish or win challenges. The nature of the rewards is later described in conjunction with FIG. 4.

As is indicated by Block 46, once an employee is entered into a challenge, the employee is left alone to live his/her life. It is hoped that the presence of the challenge and a potential reward or completing the challenge will entice the employee to exercise wherever and whenever they can. For instance, an employee may park farther away from work in order to walk a little more. The employee may take the stairs instead of the elevator. All of these little exercises are automatically recorded and are applied toward the employees challenge.

The exercise data generated by an employee is stored until the employee transfers data to the system computer 16. This can be done automatically by having the employee come within range of an office transceiver 24. However, if desired, an employee can connect the monitoring unit 20 directly to a computer at their home or office, using a standard USB connection cable. This is very useful for people who 13 work some days at home or travel often as part of their job. Once the exercise data is downloaded, the data is analyzed by the system computer 16. See Block 48. First, the data is identified according to the types of exercise preformed the data. Different exercises produce different types of data. Since the monitoring unit 20 contains accelerometers, the data gathered is analog in nature. Walking produces specific signals within the accelerometers at repeating intervals. A walking signal is straightforward to identify. Running creates greater accelerometer signals at faster intervals and is easy to identify. The signal profiles of numerous exercises are known. For instance, the signals generated by bicycle riding, swimming, and climbing stairs are readily identified. However, the signals generated by some other exercises can be identified as exercise, but cannot be precisely identified as to the type of exercise. For example, tennis and dodge ball create nearly identical signals from a monitor unit 20 worn on the foot.

As is indicated by Block 50 and Block 52, when a signal contains exercise data that cannot be specifically identified, the system computer 16 prompts the employee the next time the user logs onto the system. In the prompt, the employee is provided with a choice of exercises from which to choose. The employee is reminded of when the exercise occurred and for how long the exercise lasted. The user then selects the exercise that best fits the exercise that was recorded.

In some circumstances, the monitoring unit 20 may fail to recognize some exercise that has occurred. For instance, if an employee is wearing the monitoring unit on their foot and then goes canoeing, the monitoring unit 20 many not record any exercise even though strenuous exercise is occurring. In such situations, an employee does have the option of manually entering a specific exercise for a specific period of time. However, the exercise selected cannot be contrary to the data signals received for that period. If the selected exercise does not match the data signal, it may be assumed that the employee is lying or exaggerating and the data signal may be ignored by the system computer 16.

Once the system computer 16 has all the exercise data for a specific period of time, the system computer 16 converts the exercise data to that of the challenge exercise. See Block 54. The challenge exercise is the exercise selected by the employee when initially selecting a challenge, as indicated back in Block 44. For instance, if the selected challenge is a virtual hike, as has been previously suggested, then all exercise data is converted into walking steps. However, if the selected challenge were a virtual marathon, then all exercise data is converted into running steps. Conversion is conducted by a determination of caloric expenditure equivalency. For example, if the selected challenge exercise is walking and walking is assigned a caloric expenditure of 250 calories per mile, then swimming for fifteen minutes is converted to one mile of walking. This is because swimming for fifteen minutes also burns 250 calories, which is a caloric equivalent of one mile.

Once all the exercise data is converted into its challenge exercise equivalent, then the data is applied to the selected challenge. See Block 56. Accordingly, an employee who rides a bicycle to work and plays basketball, may quickly complete a walking challenge without ever intentionally walking for exercise.

By converting all recorded exercise data into its challenge exercise equivalency, all employees can compete toward the same goal even though they exercise in different ways. Also, various employees can compete directly with each other, even though each employee exercises in a different way.

Figure 4:
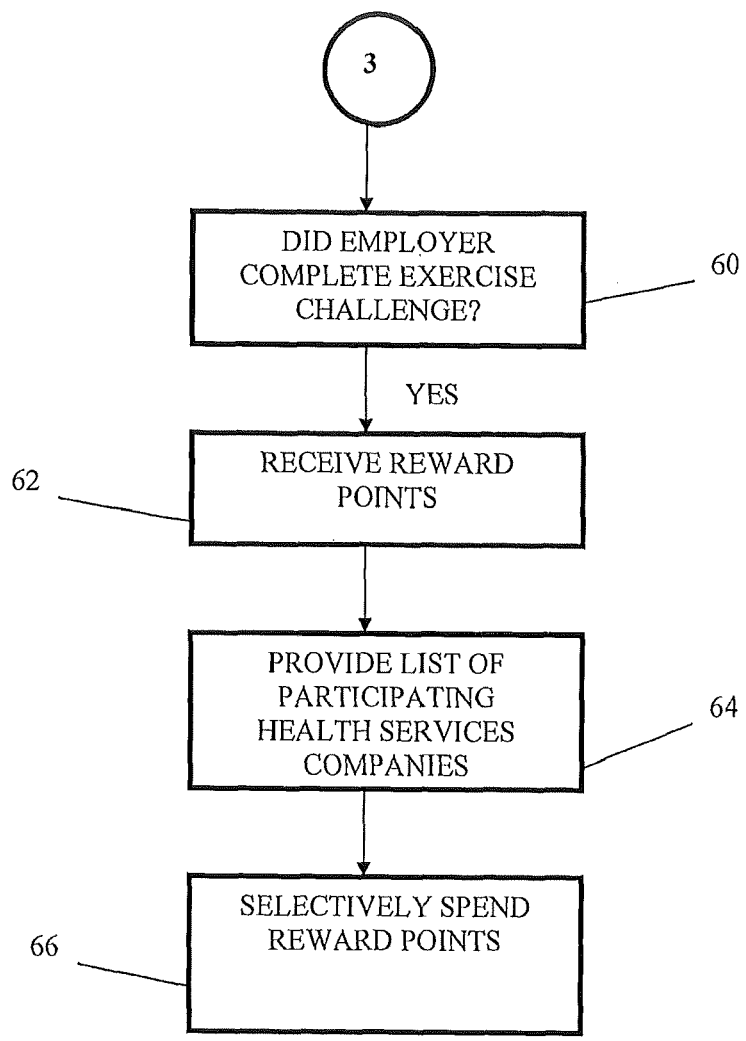
FIG. 4 is a block diagram showing a methodology of reward in accordance with the present invention system.

Referring to FIG. 4, the rewards portion of the method of operation can be outlined. As has been previously stated, an employee selects a challenge in which to participate. An employer may elect to provide rewards to the employee if the challenge is met. The rewards may be financial or work related, such as an extra vacation day. However, a unique rewards program is preferred.

As is indicated by Block 60 and Block 62, if an employee successfully completes an exercise challenge, then the employee is assigned a number of virtual reward points to his/her account. The number of reward points to be granted is directly dependent upon the difficulty of the exercise challenge that has been completed.

The administrator of the present invention system may enter into contracts with a variety of health promoting venues. The venues may include health clubs, sports clubs, sports equipment retails, vitamin retails, and the like. In these contracts, the venue companies agree to accept the virtual points awarded employees in exchange for some predetermined compensation. A list of participating companies is provided to each employee. See Block 64. The employee can then spend his/her reward points by buying the goods or services from the various participating companies. See Block 66.

By restricting the venues in which the reward points can be spent, each employee is provided a significant but limited choice. However, all the choices are beneficial to the health and well-being of the employee. It is therefore hoped that an employee's exercise will be self-perpetuating. That is, an employee earns reward points by exercising in a gym and the reward points help pay for membership in that gym. Otherwise, an employee earns reward points by playing a sport and the reward points pay for the equipment used to play that sport.

After an employee uses the present invention system for a period of time, a great deal of information is gathered concerning when and how a particular employee exercises. This information is formatted and provided to the employee for the benefit of the employee. Referring to FIG. 5, a graph 70 is shown that shows activities plotted by time and calories burned during the course of one day. The graph 70 shows only one of many ways the data can be formatted. However, when formatted as illustrated, an employee can see when they are exercising the most and when they are exercising the least. This may encourage employees to take the stairs or otherwise do some exercise during non-traditional hours.

It will be understood that the embodiment of the present invention that is illustrated and described is merely exemplary and that a person skilled in the art can make many variations to that embodiments. All such embodiments are intended to be included within the scope of the present invention as defined by the claims.

What is claimed is:

1. An exercise tracking system for tracking physical activity of a person participating in a health program, comprising:
    a server computer with a processor in data communication with a network and with a memory storing computer instructions which, when executed on the processor, implement:
        at least one health program including information of a plurality of exercise challenges, and a caloric expenditure equivalent of a plurality of physical activities;
        a user interface accessible over the network whereby a program participant is assigned a unique identification code and is associated with a select one of the exercise challenges;
    a transceiver in data communication with the server; and
    a portable monitoring unit having a unique identification code associated with the assigned participant identification code in the memory of the server and including:
        an accelerometer operable to obtain motion information of the participant;
        a clock operable to create a time code signal as time information that is associated with the motion information as it is obtained;
        a memory operable to store the motion information and time information;
        a receiver operable to receive an activation signal from the transceiver;
        a transmitter operable to send the stored motion information and time information to the server responsive to the received activation signal;
    wherein the transceiver is operable to send the motion information and time information to the server computer over the network;
    wherein the motion information and time information are analyzed by the server to determine an activity time, an activity identity, and an activity duration of physical activities performed by the participant as activity information; and
    wherein the activity information is converted to an equivalent caloric expenditure, and the caloric expenditure is converted to an equivalent amount of exercise in the exercise challenge that has the same caloric expenditure, and is correlated with the select exercise challenge to track a progress of the participant toward completion of the challenge; and
    wherein a reward is provided to the participant upon completion of the challenge.

2. The system of claim 1, wherein the challenge is a physical activity.

3. The system of claim 1, wherein the challenge includes a contest between at least two users.

4. The system of claim 1, wherein the challenge is virtual.

5. The system of claim 1, wherein a magnitude of the reward is proportional to the difficulty of the challenge.

* * * * *